United States Patent [19]

Kopito et al.

[11] 4,019,820
[45] * Apr. 26, 1977

[54] MUCUS SAMPLING AND MEASURING SYSTEMS, DEVICES AND PROCESSES

[75] Inventors: Louis Kopito, Brookline; Samuel R. Schuster, Wellesley, both of Mass.

[73] Assignee: Ovutime, Inc., Wellesley, Mass.

[ * ] Notice: The portion of the term of this patent subsequent to June 24, 1992, has been disclaimed.

[22] Filed: May 1, 1975

[21] Appl. No.: 573,730

Related U.S. Application Data

[63] Continuation-in-part of Ser. No. 399,145, Sept. 20, 1973, Pat. No. 3,891,325.

[52] U.S. Cl. .............................. 356/205; 250/574; 356/36; 356/103
[51] Int. Cl.$^2$ ........................................ G01N 21/24
[58] Field of Search ................. 250/573, 574, 576; 350/95; 356/36, 103, 201, 205, 208, 244

[56] References Cited

UNITED STATES PATENTS

| | | | |
|---|---|---|---|
| 1,480,391 | 1/1924 | Hausser | 350/95 |
| 1,940,373 | 12/1933 | Schoenberg | 250/573 X |
| 2,062,588 | 12/1936 | Logan et al. | 356/208 X |
| 2,597,425 | 5/1952 | Aiken et al. | 356/36 |

*Primary Examiner*—John K. Corbin
*Assistant Examiner*—Matthew W. Koren
*Attorney, Agent, or Firm*—Morse, Altman, Oates & Bello

[57] ABSTRACT

A mucus sample is positioned between a pair of plates at specific pressure and temperature. At least one of the plates is transparent to certain radiation and at least one of the plates is formed with ports for extrusion of the sample in order to provide a mucus stratum of predetermined thickness between the plates for measurement of optical transmissivity and/or diffusivity as an indication of the phase of the menstrual cycle.

14 Claims, 15 Drawing Figures

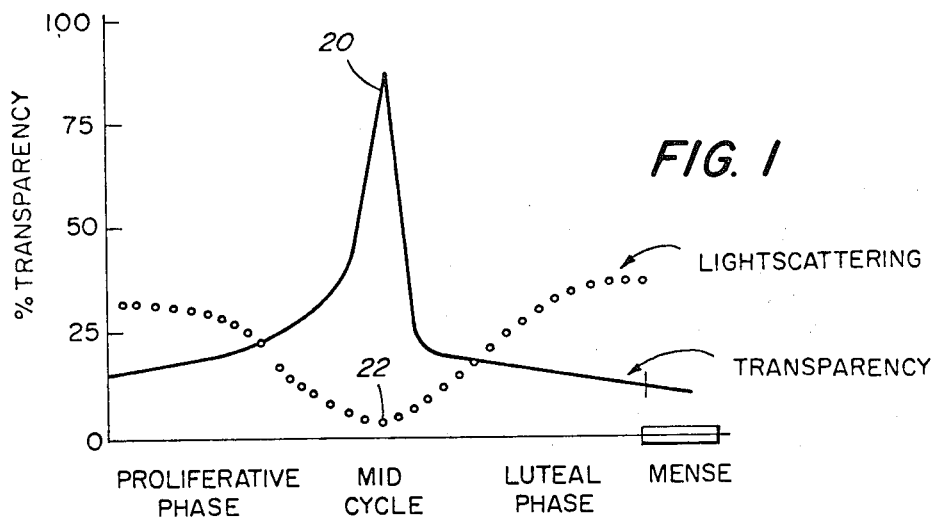
FIG. 1
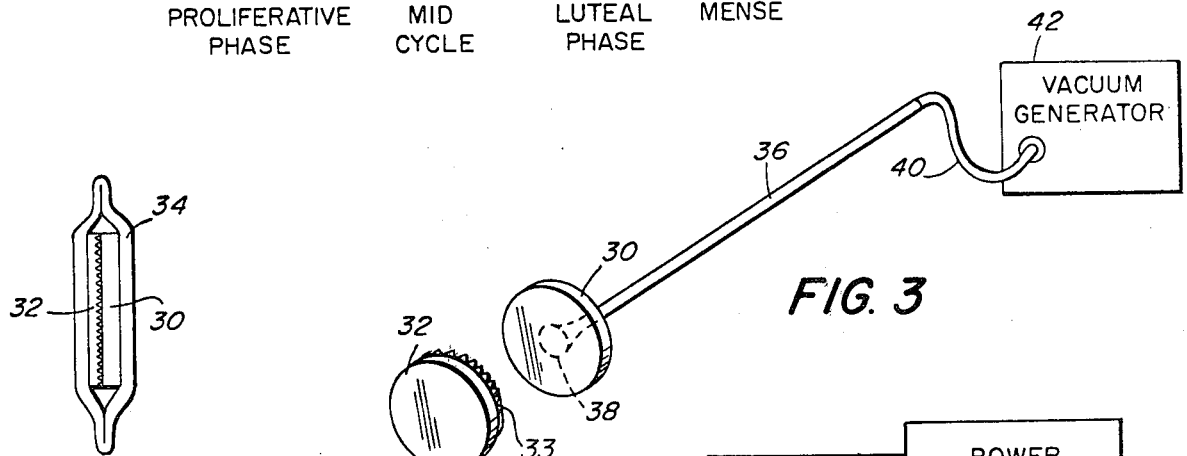
FIG. 2
FIG. 3
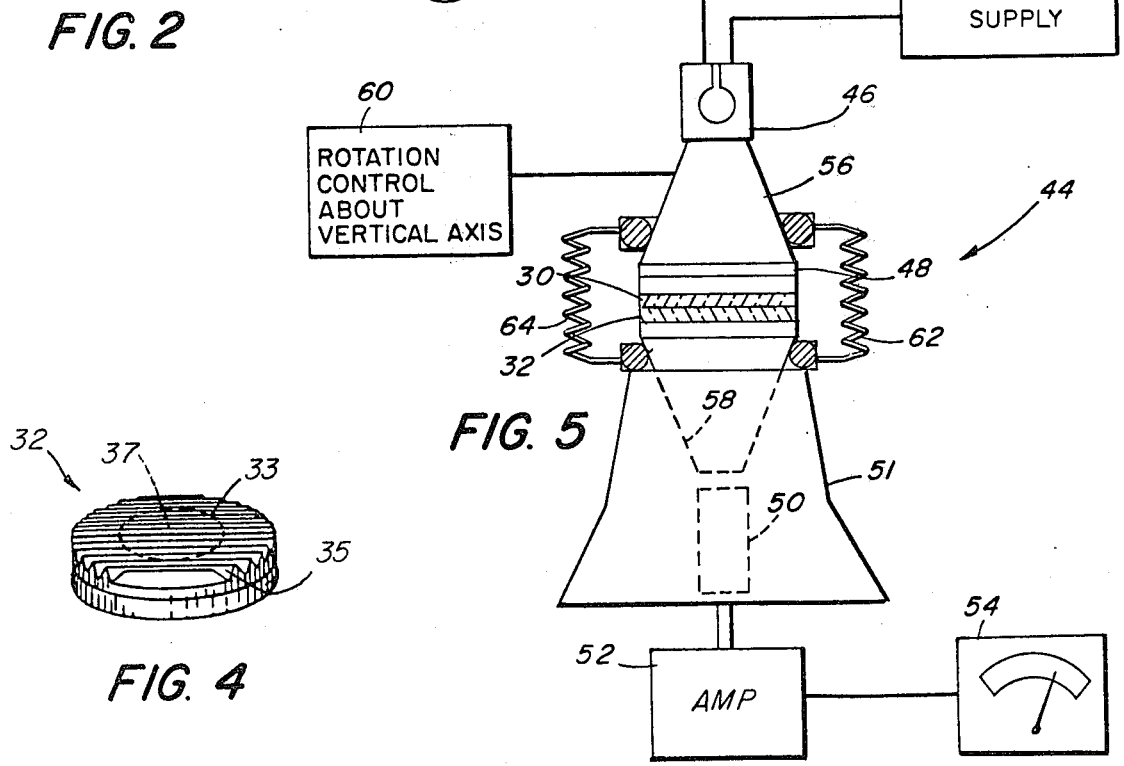
FIG. 4
FIG. 5

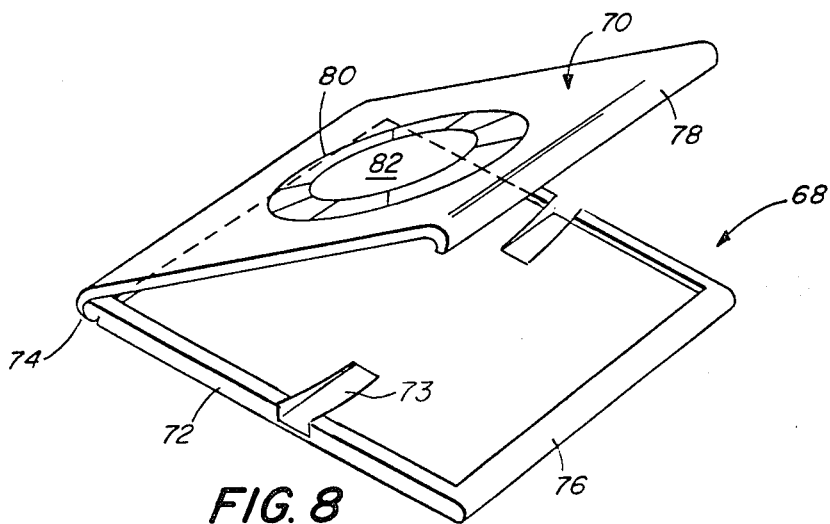
FIG. 8
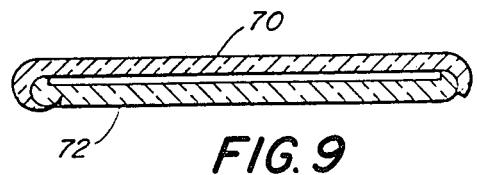
FIG. 9
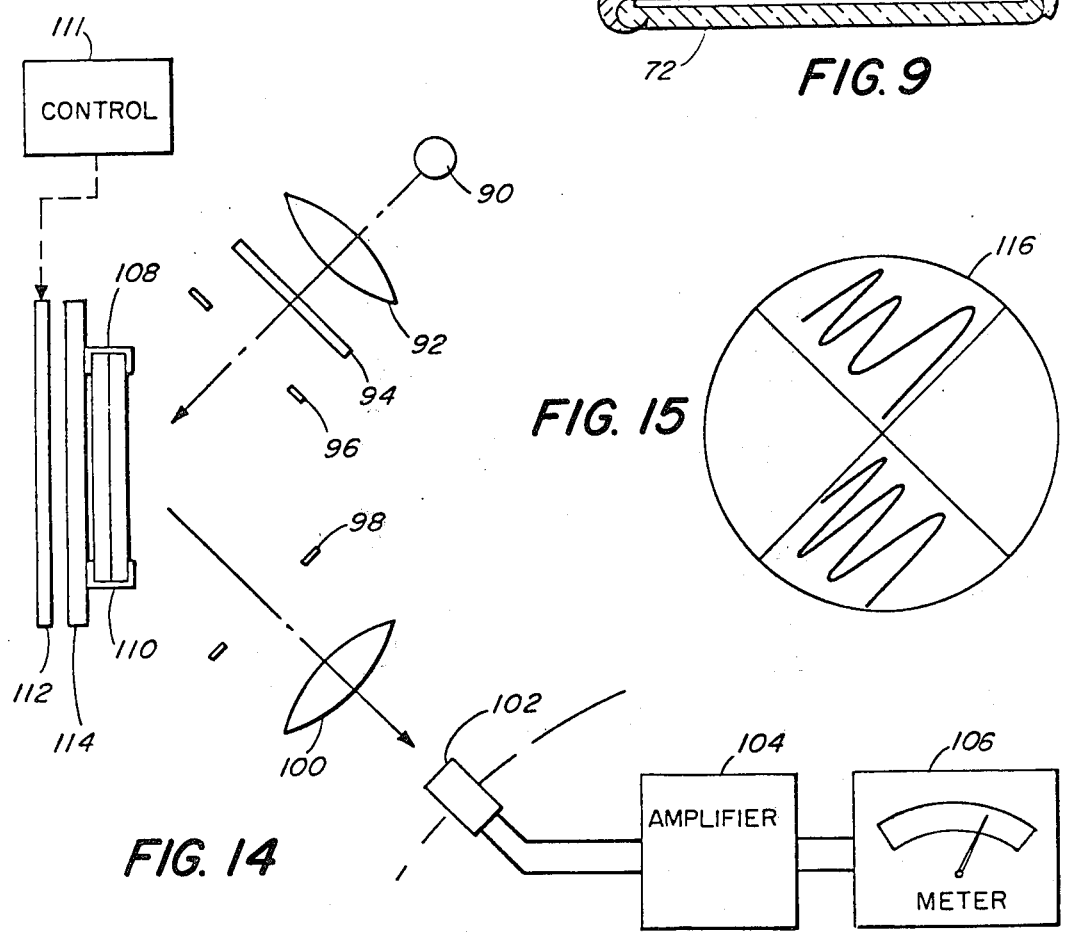
FIG. 14
FIG. 15

MUCUS SAMPLING AND MEASURING SYSTEMS, DEVICES AND PROCESSES

CROSS-REFERENCE TO RELATED APPLICATIONS

The present application is a continuation-in-part of our application Ser. No. 399,145, filed Sept. 20, 1973 for Mucus Sampling And Measuring Systems, Devices and Processes, now U.S. Pat. No. 3,891,325.

BACKGROUND OF THE INVENTION

1. Field of Invention

The present invention relates to systems, processes and products for determining the phase of the menstrual cycle and particularly to measurement of transparency and/or diffusivity of bodily mucus, particularly cervical and/or oral mucus in order to predict and to indicate the inception and the presence of ovulation for conception control.

2. Description of the Prior Art

It has been found that mucus sampled from the vaginal and oral cavities undergoes distinct physical and chemical changes during the menstrual cycle. For example, cervical mucus, a hormonally controlled secretion, is produced continuously, varying in quantity, composition and physical properties during the menstrual cycle. In the cervical canal, the anatomic connection between the vaginal lumen and the uterine cavity, the mucus secreted by the cervical glands acts as a mechanical and biochemical barrier against intruding organisms, including male spermatozoa. During the preovulatory phase, under estrogen domination, the mucus is profuse, watery, optically clear, alkaline and favorable to sperm penetration. During the postovulatory, progestational phase, the mucus changes remarkably becoming less abundant and fluid, more optically opaque, and less alkaline or slightly acidic. During this phase, the cervical mucus, which contains an increased number of leukocytes and other cellular components, is practically impenetrable to spermatozoa. In healthy women with normal menstrual cycles, as is well documented in the medical literature, ovulation usually occurs between the 12th and 14th day prior to the next menstrual period. Determining ovulation on the basis of the preceeding menstrual period, such as in the rhythm method of counting the days ellapsed between the termination of the menstrual period and the presumed mid-cycle ovulatory phase, is prone to errors because of the great variability in the length of the proliferative period, i.e. between the end of the menses and ovulation. Although it is possible to predict ovulation on the basis of hormonal changes in the blood or chemical changes in the mucus, present procedures for analyzing such changes are useful only in special cases, because of the laboratory time and high cost required to perform analyses, which may take from several days to two weeks. By the time the results are available to the gynecologist, about half of the menstrual cycle may have elapsed. At the present time, there are no known reliable on-the-spot techniques capable of providing the information necessary for prediction or confirmation of ovulation during or immediately after examination of a patient.

It is known also that several optical properties of cervical mucus change considerably during the menstrual cycle. These properties include index of refraction, transparency (transmittance) to white light and to light of selected wavelengths, and diffusivity. The most important single factor determining the degree of transparency of mucus is water concentration. The mucus is most hydrated at the time of ovulation, containing 97 to 98% water. At other times during the menstrual cycle, the mucus is relatively dehydrated, containing only 80 to 90% water. The solids or non-volatile residue remaining in the mucus after desiccation may range from 2% to 20% of the weight of fresh mucus, representing as much as a 10 fold increase between the time of ovulation and other periods in the cycle. The solid residue consists primarily of proteins, salts, carbohydrates, lipids, exfoliated cellular elements and other organic materials, such as bacteria. The major mucus fraction is a carbohydrate rich glycoprotein, which accounts for 70 to 80% of the dry residue. The remaining fraction essentially includes 20 to 30% aminoacid residues, as well as sodium chloride and other inorganic salts. Protein concentration varies considerably during the menstrual cycle, ranging from about 40 to 50 mg per gram of total weight during the proliferative and luteal phases to about 3.5 mg per gram of total weight at ovulation. Electron-microscopic studies of cervical mucus show that, at mid-cycle, mucus consists primarily of clusters of globular particles, 1000 to 1500 A in diameter, connected by thin string-like strands of material. In the early luteal phase, these mucus strands are considerably enlarged to about 200 A in diameter, creating an interlocking mesh without spherical components. It is believed that the change in structure that accompanies decrease in protein concentration at mid-cycle, coupled with an increase in water, renders the mucus transparent at that time. At the other times during the menstrual cycle, the mucus becomes increasingly opaque as a function of the concentration of proteins and cellular debris. A need has arisen for improvements in devices and processes which utilize the foregoing for the purpose of determining ovulation.

SUMMARY OF THE INVENTION

The primary object of the present invention is to provide devices and processes for determining the phase of the menstrual cycle. Generally, the device comprises a pair of plates, at least one of the plates is transparent to certain radiation and at least one of the plates is formed with ports. A mucus sample is positioned between the plates at specific pressure and temperature in order to provide a mucus stratum of predetermined thickness between the plates, excess mucus being extruded through the ports. A photometer assembly is provided for measuring the optical transmissivity and/or diffusivity in order to determine the phase of the menstrual cycle.

Other objects of the present invention will in part be obvious and will in part appear hereinafter.

The invention accordingly comprises the processes, products and devices, together with their steps, parts, components and interrelationships, which are exemplified in the present disclosure the scope of which will be indicated in the appended claims.

BRIEF DESCRIPTION OF DRAWINGS

For a fuller understanding of the nature and objects of the present invention, reference is made to the following detailed description which is to be taken in connection with the accompanying drawings, wherein:

FIG. 1 is a graph illustrating certain principles of the present invention;

FIG. 2 illustrates, in cross section, a product useful in accordance with the present invention;

FIG. 3 illustrates, in perspective, a device for applying the product of FIG. 2;

FIG. 4 is a perspective of the thickness control plate of FIG. 3;

FIG. 5 is a schematic view of a device for performing certain steps in accordance with the present invention;

FIG. 8 is a perspective view of yet another product of the present invention, in an inoperative condition;

FIG. 9 is a cross-sectional view of the product of FIG. 8, in an operative condition;

FIG. 14 is a schematic view of another device for performing certain steps in accordance with the present invention; and FIG. 15 is a plan view of a component of the device of FIG. 14.

DETAILED DESCRIPTION OF THE PREFERRED EMBODIMENTS

Figure 6:
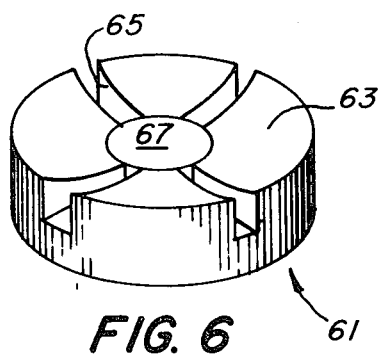
FIG. 6 is a perspective view of a product of the present invention.

The graph of FIG. 1 illustrates certain properties of cervical mucus during the typical menstrual cycle of a normal woman, showing peak transparency 20 at ovulation. At the same time, the minimum amount of light scattering 22 results from the reduced presence of cellular material. During the proliferative phase, the transparency of the mucus increases gradually until three of four days before ovulation when more rapid day to day increases occur. The maximum transparency is reached on the day of ovulation when the mucus is nearly 90% transparent to white light. A sharp increase in opacity occurs one or two days following ovulation and continues at a much slower rate during the remainder of the cycle. These physio-optical changes in cervical mucus in the past, have been detected by simple visual estimation.

FIGS. 2, 3, 4 and 5 illustrate a preferred system incorporating the present invention for measurement of optical transmissivity and/or diffusity in order to provide an indication of the phase of the menstrual cycle. The critical aspects of the measurement of the optical properties of a mucus sample, for example cervical mucus, is the thickness of the mucus stratum. According to Beer's law, each individual molecule of the absorbing mucus stratum absorbs the same fraction of the radiation incident upon it. The effects of thickness L of the specimen or length of path and concentration C of the specimen to be measured on absorption of radiation can be expressed as $$I/I_o = 10^{-KCL}$$

where $I$ is the intensity of the transmitted radiation, $I_o$ is the intensity of the incident radiation, and K (extinction coefficient) is a constant that is dependent on the concentration of the mucus and wavelength. In logarithmic form, $$\log I/I_o = A = abc$$

where A is absorbance, $a$ is absoptivity, $b$ is path length, and $c$ is concentration.

It is preferred that the measurements are obtained with 20% to 70% transmittance in order to minimize errors. For example, the expected error at 90% transmittance is ± 3% and the expected error at 99% transmittance can be 33%. For reasons of accuracy and reproducibility, the dimensions of the mucus sample provided by the invention does not vary from specimen to specimen. The thickness of the mucus sample obtained by the device of the present invention is such that the absorbance range is 20% to 70% between the time of ovulation and other periods of the menstrual cycle.

Referring now to FIG. 3, mucus specimens are collected on a disc 30 typically 2.0 mm to 5.0 mm thick and 15 mm to 30 mm in diameter. Disc 30, which defines a mucus collecting plate, is composed of a sterilizable material, for example glass or methyl methacrylate. Associated with disc 30 is a disc 32, which defines a thickness control plate. As best shown in FIG. 4, a working face of disc 32 is formed with a plurality of prismatic ridges 33, which are etched, milled or hot pressed. Ridges 33, which are in spaced parallel relationship to one another, occur at a rate in the range of 3 per cm to 80 per cm and have a depth in the range of 0.002 mm to 0.3 mm. A trough 35 is formed between each of ridges 33, each trough defining a port through which the mucus specimen is extruded when discs 30 and 32 are pressed together. Disc 32, which is typically 2.0 mm to 5.0 mm thick and 15 mm to 30 mm in diameter, is composed of a sterilizable material, for example glass or methyl methacrylate.

As shown in FIG. 2, discs 30 and 32 are supplied in a sterilized hermetic package composed of, for example, waxed paper or plastic, After riping open package 34, disc 30 is held by a hollow stainless tube 36, which is easily sterilizable. Tube 36 is provided with a suction cup 38 at one end and a hose 40 at the other end. Hose 40 is connected to a vacuum generator 42. Mucus is obtained by pressing and rotating disc 30 lightly against the cervical os. Disc 32 then is superposed on and pressed against disc 30 with the mucus sample therebetween. The configuration of the working face of disc 32, i.e. the prismatic ridges, is such that an exact amount of mucus is extruded in each trough 35 and the thickness of the remaining mucus stratum is controlled by the sharp top edges of the ridges. The extruded specimen is forced out of the open ends of the troughs 35. Since dehydration of the specimen is one of the critical variables in determining the menstrual cycle phase, the measurement is confined to a central section 7 of disc 32, for example a central circular section having a diameter of approximately 6.0 mm to 13 mm. The mucus stratum contained within section 37 is protected from evaporation by the more distant mucus sample. Preferably, the time lapse between obtaining the mucus sample and pressing it between the discs is no more than 30 to 60 seconds in order to prevent evaporation and contamination. The superposed disc and mucus sample assemblage now is placed inside the special photometer assembly 44 illustrated in FIG. 5.

Photometer assembly 44 comprises a light source 46, a light filter 48 to transmit selected wavelengths, and a detector 50 to provide electronic signals for amplification at 52 and a display at 54. In accordance with the present invention, a conical fiber optic bundle 56 serves as a diverging collimator and a conical fiber optic bundle 58 serves as a converging decollimator. A housing 51 is provided to shield detector 50 from stray light. The use of fiber optics rather than conventional optics has the following advantages: the light source is located at a fair distance away from the measuring head, thereby preventing heating of the specimen by which its physical composition might be changed; the matching surfaces of the fiber optic devices are selected in a manner to provide maximum resolution for the detection of cellular components. For example, an assembly of 20 micron fibers will resolve 22 lines/mm while an assembly of 6 micron fibers will resolve 90 lines/mm. By relatively rotating the faces of the fiber optic bundles 56, 58, by a suitable control 60, the fibers may be registered to provide maximum transmission, de-registered to provide minimum transmission, or adjusted to provide intermediate transmission. When assemblage 30, 32 is in position between the faces of fiber optic bundles 56, 58, these two faces are pressed against the opposite faces of the assemblage by biasing springs 62, 64, which exert a uniform pressure between the discs ranging from 3 to 30 pounds per square inch. It has been found that, within this pressure range and at a temperature range of between 60° to 100° F., the thickness of the mucus sample falls within the range of 0.005 to 0.2 mm.

Figure 7:
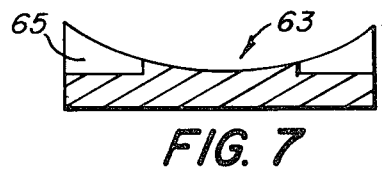
FIG. 7 is a cross-sectional view of the product of FIG. 6.
Figure 10:
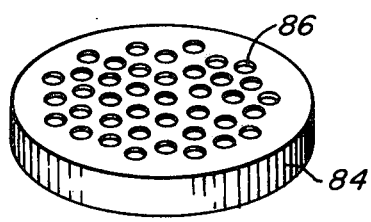
FIG. 10 is a perspective view of a product of the present invention for dry mucus.
Figure 11:
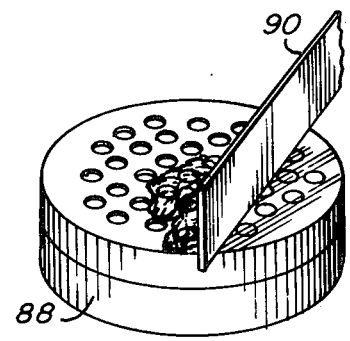
FIG. 11 is a perspective view of the product of FIG. 10 in operation.

Referring to FIGS. 6 and 7, there is shown an alternate embodiment of thickness control plate 32, in the form of a disc 61 having a concave working surface 63. Disc 61 is composed of, for example, a polymer such as methyl methacrylate. A plurality of ports 65, which define ports through which the mucus specimen is extruded, extend inwardly from the outer periphery of disc 61 to a central section 67. In the illustrated embodiment of FIGS. 6 and 7, each port 65 is approximately 1 mm to 5 mm wide and 0.5 mm to 2.5 mm deep and section 67 is 6.0 to 13 mm in diameter. Preferably, the mucus sample is deposited in central section 67 in a circular pattern.

An alternative product embodying the present invention is shown in FIGS. 8 and 9 as comprising an assemblage 68 of a pair of plates 70, 72, which are composed, for example, of a polymer such as methyl methacrylate. Plates 70, 72 are pivoted to each other at one edge 74 of the assemblage. At the opposite end, plate 72 has a rounded extremity 76 and plate 70 has a hooked extremity 78. Hooked extremity 78 and rounded extremity 76 are mated so that the two plates manually can be snapped into locked condition with inner faces apart. The inner face of plate 72 has a planar depression, ranging in depth from 0.005 mm to 0.2 mm for the reception of a mucus sample and is formed with ports 73 through which excess mucus is extruded. The inner face of plate 70 has an annular sequence of light absorbing areas 80 surrounding a clear area 82. Areas 80 are characterized by incremental absorptivities so that when the plates are snapped into closed operative condition with a mucus sample, as seen through clear region 82, with the incremental absorptivities of areas 80 enable a determination approximate absorptivity of the sample by transmitted or reflected light.

Figure 12:
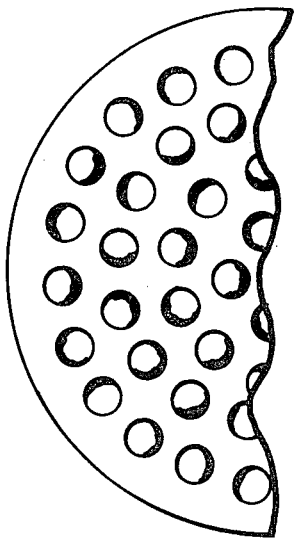
FIG. 12 is a top plan view, somewhat enlarged, illustrating certain principles of the present invention.
Figure 13:
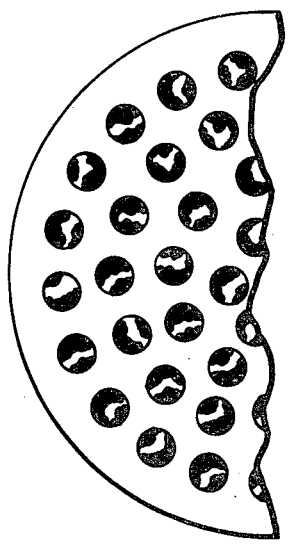
FIG. 13 is a top plan view, somewhat enlarged, illustrating certain principles of the present invention.

In an alternative embodiment, a dry mucus sample is utilized during the measurement process instead of the wet mucus sample hereinbefore described. The dry mucus sample provides optical properties at mid-cycle that are readily distinguishable from the optical properties exhibited at other times during the menstrual cycle. As previously discussed, the major component of cervical mucus is water. At mid-cycle, near the time of ovulation, the water content of the mucus is approximately 98% and the solid content is approximately 2%. At other times during the menstrual cycle, the water content of the mucus is approximately 75% to 85%. In the case of wet mucus, it is necessary to distinguish between a sample having a water content of approximately 80% and a sample having a water content of 98%. In the case of dry mucus, it is necessary to distinguish between a sample having a solid content of 2% and a sample having a solid content of approximately 20%, a ten fold difference. In the wet mucus embodiment shown in FIG. 10, 11, 12 and 13, a mucus sample is deposited on a plate 84 that is formed with a plurality of through holes 86. In one embodiment, plate 84 is composed of a metal such as stainless steel and holes 86 are formed by a photoetching process. Holes 86, whch have a diameter in the range of 0.02 mm to 2.6 mm and a depth in the range of 0.02 mm to 2.6 mm, occur at a rate in the range of $1/cm^2$ to $5/cm^2$. In order to assure an even thickness of mucus and to fill all of holes 86, plate 84 is placed on a glass disc 88 and excess material is wiped off with a scraper 90, for example a glass microscope slide. Then, the mucus is dried by means of a hot air blower or a hot plate (not shown). The dried mucus fills a part of each hole. As shown in FIG. 12, approximately 2% of each hole 86 is covered by the high water content mid-cycle mucus. On the other hand, approximately 20% of each hole 86 is covered by the mucus at the other times of the menstrual cycle as illustrated in FIG. 13. Then, plate 84, which contains the dried mucus, is positioned between the faces of optic bundles 56 and 58. Preferably, photometer assembly 44 is calibrated to read "0" absorption (100% transmission) on display 54 without a sample. At this calibration, the reading on display 54 will be approximately 2% for dried mid-cycle mucus and approximately 20% for dried mucus at other times during the menstrual cycle. Amplifier 52 is adjusted for a gain of 10 in order to utilize a scale reading from 0 to 100 on display 54. A scale reading of 20% is indicative of mid-cycle ovulation and a scale reading of 100% is indicative of non-ovulatory periods. Of special interest are scale readings in the range of 20% to 60%.

The system of FIG. 14 is based on the following considerations. Because cellular material is nearly absent in cervical mucus just at the time of ovulation and because it is present at other times during the cycle, it is possible to enhance the determination of transparency by also measuring light scattering. It is estimated that light scattering of the mucus is about 2% to 5% at mid-cycle while at pre- and post-ovulatory periods it may amount in excess of 30%. Thus, measuring light scattering alone may provide a range of about 15 to 1 whereas the measurement of absolute transparency may provide a range of about 5 to 1. Using both measurements together enhances the overall result and provides, without additional sampling, a double indication of ovulation by two nearly independent variables. All of the components of the system of FIG. 14 are enclosed within a suitable housing (not shown).

FIG. 14 shows a spectrophotometer that is designed to measure the quantity of light transmitted through the specimen as well as the amount of scattering produced by the presence of cellular components. The two measurements are taken without removing the sample cell from the spectrophotometer. The illuminating subassembly includes a light source 90, a collimating lens 92, a selected band pass filter 94, and an adjustable aperture 96. The detecting sub-assembly comprises an adjustable aperture 98, a collimating lens 100, a detector 102, an amplifier 104, and a meter readout 106. The sample assemblage is collected between two glass discs (described previously in connection with FIGS. 3, 4, 5 and 6), which are spring pressed together by spring clips 108, 110 in order to achieve reproducible thickness. The sample assemblage is backed by a mirror 112. The meter is calibrated to read from 0% to 100%, using a reference set of glass discs at position 114 without the sample cell in position. After calibration, the sample cell is inserted and the amount of light transmitted is read. Then, under a control 111, mirror 112 is rotated out of the optical path and a second reading, that of the energy reflected by scattering is taken. The final value is a function of the ratio of the two readings as follows:

Light transmitted (T)/Light scattered (S) = resultant value

At ovulation the light transmitted (T) is at maximum, the mucus being most transparent at that time and the light scattered (S) is minimal at ovulation. Hence the resultant value of the ratio of the two (T/S) yields a relatively large number, typically 90/2=45. At other times during the cycle the mucus is relatively opaque and the quantity of cellular material is high. Hence T/S yields a relatively small number, typically 10 to 80/5 to 30 = 1/3 to 16.

In one embodiment, the photometer of FIG. 14 may be programmed to yield a single relative value of T/S at optimal conditions. This value ordinarily ranges from 80 to 100 at ovulation and from 0.5 to 35 or 50 at other times. These values are arbitrary indicators designed to give maximum separation between approaching ovulation, the actual event, and confirmation, one day later. As an added refinement, a chopper 116, which is illustrated in FIG. 15, may be introduced to replace mirror 112, yielding an AC signal. This mirrored chopper provides two measurements of scattering and two measurements of transparency per cycle. The resulting signal is processed to yield the T/S value described above. This signal is recorded on a time basis to obtain another value relating to the evaporation of the water from the mucus under controlled conditions. At midcycle, the mucus contains more water than at the other times so that the decay curve will be of longer duration. At other times in the cycle the decay curve will be of lesser duration.

The present invention departs from previous theories which stress the need for measuring "true" physical properties such as the index of refraction. The present device is not intended primarily to produce a physical measurements relating to homogenous fluids. Instead, the property measured by the present system utilizes biological changes which contribute to the non-ideal physical properties of cervical mucus, i.e. cellular inclusions and ultrastructural changes induced by the polymerization of the glycoproteins, all of which differentiate the phase of ovulation from other phases of the menstrual cycle. Hence, the property actually measured, expressed in a numerical value not related to a defineable single physical concept, is related to a sum total of most of the interacting physiochemical events.

Acting together, these events create a complex material of predictable optical behavior during the menstrual cycle. The instrument in various forms is designed to give a numerical value in the range of 0 to 100 (or higher if necessary) to provide the practical means for sensing oncoming ovulation and pin-pointing this event. It takes advantage of the wide range of optical properties of the mucus, from near complete transparency with little scattering at ovulation to reduced transparency with considerable scattering of light at other times during the menstrual cycle.

Since certain changes may be made in the present disclosure without departing from the scope of the invention thereof, it is intended that all matter described in the above specification or shown in the accompanying drawings be interpreted in an illustrative and not in a limiting sense.

What is claimed is:
1. A process for determining the phase of a menstrual cycle, said process comprising the steps of contacting a face of a first plate with a sample of bodily mucus, superposing a face of a second plate on said face of said first plate and uniformly applying a pressure across said plates to produce a mucus stratum between said faces, at least one of said plates being at least partially transparent to certain radiation, at least one of said plates being formed with a port through which excess bodily mucus is extruded, transmitting said radiation through said transparent plate and said mucus stratum in order to produce an indication functionally related to absorptivity of said mucus stratum with respect to said radiation, and processing said indication to a form representative of said phase of said menstrual cycle.

2. The process of claim 1 wherein said mucus is cervical.

3. The process of claim 1 wherein said plates are substantially transparent.

4. The process of claim 1 wherein a reflector is in optical alignment with the other of said plates.

5. The process of claim 1 wherein said indication functionally related to absorptivity is a function of the ratio of absorptivity to diffusivity.

6. A system for determining the phase of a menstrual cycle for use with a first plate and a second plate, said system comprising first means for contacting one face of said first plate with a sample of bodily mucus, second means for uniformly applying a pressure across said first plate and said second plate when superposed, said pressure ranging from 3 to 30 pounds per square inch to produce a mucus stratum between said faces, at least one of said plates being at least partially transparent to certain radiation, at least one of said plates being formed with a port through which excessive bodily mucus is extruded, and third means for transmitting said radiation through one of said plates and said mucus stratum in order to produce a signal functionally related to absorptivity of said mucus stratum with respect to said radiation.

7. The system of claim 6 wherein said first means includes a vacuum cup for contacting said first plate, a probe having a conduit communicating with said vacuum pump communicating with said conduit.

8. The system of claim 6 wherein said second means includes resilient spring means.

9. The system of claim 6 wherein said third means includes a light source, a diverging fiber optical bundle extending form said light source to said pair of plates, a detector, and a converging fiber optics bundle extending from said pair of plates to said detector.

10. The system of claim 6 wherein said third means includes a light source path obliquely disposed with respect to said pair of plates, a removable reflector backing said plates, and a detector path obliquely disposed with respect to said pair of plates.

11. The system of claim 10 wherein said reflector is moving and has alternate absorbing and reflecting regions in order to constitute a chopper.

12. The system of claim 6 wherein said one plate formed with ports is a plate having a plurality of prismatic ridges on a working face thereof, troughs being formed between adjacent ridges, said troughs defining ports through which said excessive bodily mucus is extruded.

13. The system of claim 12 wherein said prismatic ridges occur at a rate in the range of 3 per cm to 80 per cm and have a depth in the range of 0.002 mm to 0.3 mm.

14. The system of claim 6 wherein said one plate formed with ports has a concave working surface, said ports extending inwardly from the outer periphery to a central section.

* * * * *